US012128162B2

(12) United States Patent
Shackle

(10) Patent No.: US 12,128,162 B2
(45) Date of Patent: Oct. 29, 2024

(54) ULTRAVIOLET RADIATION AIR SANITIZING MACHINE

(71) Applicant: Kevin Shackle, Stillwater, MN (US)

(72) Inventor: Kevin Shackle, Stillwater, MN (US)

(*) Notice: Subject to any disclaimer, the term of this patent is extended or adjusted under 35 U.S.C. 154(b) by 0 days.

(21) Appl. No.: 17/652,768

(22) Filed: Feb. 28, 2022

(65) Prior Publication Data

US 2022/0273838 A1 Sep. 1, 2022

Related U.S. Application Data

(60) Provisional application No. 63/154,984, filed on Mar. 1, 2021.

(51) Int. Cl.
| | |
|---|---|
| *B01D 45/12* | (2006.01) |
| *A61L 9/20* | (2006.01) |
| *B04C 3/06* | (2006.01) |
| *B04C 9/00* | (2006.01) |
| *B04C 3/00* | (2006.01) |

(52) U.S. Cl.

CPC ................ *A61L 9/20* (2013.01); *B01D 45/12* (2013.01); *B04C 3/06* (2013.01); *B04C 9/00* (2013.01); *A61L 2209/14* (2013.01); *B04C 2003/003* (2013.01)

(58) Field of Classification Search
CPC .......... A61L 9/20; A61L 2209/14; A61L 2/10; B01D 45/12; B01D 45/16; B04C 3/06; B04C 9/00; B04C 2003/003; B04C 2009/007; B04C 5/13; B04C 5/08; F24F 8/22; A47L 11/405
See application file for complete search history.

(56) References Cited

U.S. PATENT DOCUMENTS 3,105,733 A 7/1961 Potapenko
3,518,046 A 9/1968 Cicirello
5,456,837 A * 10/1995 Peachey .................... B04C 5/28 210/512.2
5,505,904 A 4/1996 Haidinger et al.
5,997,619 A 12/1999 Knuth et al.
6,589,323 B1 * 7/2003 Korin ..................... B01D 53/04 55/459.1
8,431,098 B2 * 4/2013 Anderson ............ B01D 53/864 422/4
9,974,881 B2 5/2018 Kim et al.
10,323,851 B2 6/2019 Huang et al.

(Continued)

FOREIGN PATENT DOCUMENTS

EP 1688151 A1 8/2006
EP 2344353 B1 8/2014

(Continued)

*Primary Examiner* — Dung H Bui
(74) *Attorney, Agent, or Firm* — Sherrill Law Offices, PLLC

(57) ABSTRACT

An ultra violet air disinfectant machine 100 that includes a cyclone separator 120 configured and arranged for effecting a spiral vortex flow of air through a disinfection chamber 129 about a longitudinal axis x operable for inertial concentration of microbes in the spiral vortex flow of air proximate a sidewall **122*s* of the cyclone separator 120, and a source of germicidal ultraviolet radiation 140 positioned external to the disinfection chamber 129 for emitting germicidal ultraviolet radiation towards and into the disinfection chamber 129**.

24 Claims, 2 Drawing Sheets

(56) References Cited

U.S. PATENT DOCUMENTS

| | | |
|---|---|---|
| 10,717,043 B2 | 7/2020 | Lv et al. |
| 2005/0016378 A1 | 1/2005 | Yuen |
| 2005/0035301 A1 | 2/2005 | Wang |
| 2005/0163648 A1 | 7/2005 | Liang |
| 2006/0130447 A1* | 6/2006 | Seo .................. B01D 45/16 55/426 |
| 2006/0201119 A1* | 9/2006 | Song .................. B01D 53/007 55/471 |
| 2007/0209147 A1* | 9/2007 | Krebs .................. A47L 9/1641 15/347 |
| 2007/0253874 A1* | 11/2007 | Foret .................. B04C 5/103 204/176 |
| 2007/0266678 A1* | 11/2007 | Makarov .................. B04C 5/13 55/337 |
| 2008/0075627 A1* | 3/2008 | Garin .................. A61L 9/18 422/4 |
| 2008/0279733 A1 | 11/2008 | Glazman |
| 2008/0289139 A1* | 11/2008 | Makarov .................. A47L 9/1683 15/350 |
| 2008/0295271 A1* | 12/2008 | Perunicic .................. A47L 11/405 15/246.3 |
| 2010/0047117 A1* | 2/2010 | Bernard .................. A61L 9/205 422/4 |
| 2011/0250099 A1* | 10/2011 | Bagwell .................. F24C 15/2035 422/186.3 |
| 2012/0036675 A1* | 2/2012 | Conrad .................. A47L 9/1625 15/347 |
| 2012/0096670 A1* | 4/2012 | Kim .................. A47L 9/0477 96/225 |
| 2012/0246863 A1 | 10/2012 | Douglas |
| 2013/0017135 A1* | 1/2013 | Anderson .................. B01D 53/8668 423/210 |
| 2014/0366314 A1* | 12/2014 | Conrad .................. A47L 5/225 15/353 |
| 2015/0000077 A1* | 1/2015 | Conrad .................. A47L 9/1666 15/344 |
| 2019/0015780 A1* | 1/2019 | Lv .................. B01D 53/04 |
| 2019/0099705 A1* | 4/2019 | Howe .................. B01D 53/265 |
| 2019/0283046 A1* | 9/2019 | Jung .................. B04C 11/00 |
| 2022/0112704 A1* | 4/2022 | Garrels .................. A61L 2/22 |
| 2022/0218865 A1* | 7/2022 | Doyle .................. A61L 2/10 |

FOREIGN PATENT DOCUMENTS

| | | | | |
|---|---|---|---|---|
| EP | 2443977 B1 | 12/2018 | | |
| WO | 02/076517 A1 | 10/2002 | | |
| WO | 03/037389 A1 | 5/2003 | | |
| WO | 03/059821 A1 | 7/2003 | | |
| WO | WO-2004101162 A1 * | 11/2004 | ............... | A61L 2/10 |
| WO | 2005/082486 A1 | 9/2005 | | |
| WO | 2016/137550 A1 | 9/2016 | | |
| WO | 2017/188915 A1 | 11/2017 | | |

\* cited by examiner

ULTRAVIOLET RADIATION AIR SANITIZING MACHINE

BACKGROUND

Ultraviolet radiation, and in particular the high strength portion of utraviolet radiation known as UVC, is known to kill microorganisms including disease causing viruses and bacteria.

UVC is also harmful to humans, and is particularly damaging to the eyes. Hence, design of an ultraviolet air sanitizer machine must carefully consider the extent of any UVC emissions that escape the machine when the machine is to be used with humans present.

Many different compact, self-contained ultraviolet air sanitizer machines have been developed over the years in an attempt to achieve destruction of airborn microbes within a given room, with mixed results.

Prior designed compact, self-contained ultraviolet air sanitizer machines have proven to be ineffective for achieving a reasonable degree of sanitization throughout a room of any size, either as a result of insufficient air flow through the machine and/or an insufficient time of exposure to the UVC radiation.

A continuing need exists for a compact, self-contained, ultraviolet air sanitizer machine capable of effectively and efficiently microbially sanitizing the air in a room while humans occupy the room.

SUMMARY OF THE INVENTION

The invention is an ultra violet air disinfectant machine. The machine includes a cyclone separator and at least one source of germicidal ultraviolet radiation.

In one embodiment the cyclone separator has a housing that defines a disinfection chamber configured and arranged for effecting a spiral vortex flow of room air within the disinfection chamber about a longitudinal axis of the disinfection chamber. The spiral vortex effects an inertial concentration of the relatively heavy microbes in the air proximate a sidewall of the cyclone separator. The at least one source of germicidal ultraviolet radiation is positioned external to the housing for emitting germicidal ultraviolet radiation towards and into the disinfection chamber.

In another embodiment the cyclone separator has a housing that defines a cylindrical or conical disinfection chamber with a smoothly curved inner sidewall surface. The disinfection chamber is configured and arranged for effecting a spiral vortex flow of room air within the disinfection chamber about a longitudinal axis of the disinfection chamber. The smoothly curved inner sidewall surface of the housing promotes laminar flow or air within the spiral vortex. The at least one source of germicidal ultraviolet radiation is positioned external to the housing for emitting germicidal ultraviolet radiation towards and into the disinfection chamber.

DETAILED DESCRIPTION OF A PREFERRED EMBODIMENT

| Nomenclature Table | |
|---|---|
| REF. NO. | DESCRIPTION |
| 100 | Ultra Violet Air Disinfectant Machine |
| 120 | Cyclone Separator |
| 122 | Housing |
| $122R^1$ | Internal Radius of Housing |
| 122s | Inner Sidewall Surface of Housing |
| 124 | Sidewall of Housing |
| 126 | UVC Transparent Window |
| 129 | Disinfection Chamber |
| 129p | Proximal End of Disinfection Chamber |
| 129d | Distal End of Disinfection Chamber |
| 129t | Radial Thickness of the Disinfection Chamber |
| 140 | UVC Bulb |
| 160 | Fan |
| 180 | Shroud |
| 190 | Exhaust Tube |
| 190i | Inlet End of Exhaust Tube |
| 190ii | Outlet End of Exhaust Tube |
| $190r^1$ | Internal Radius of Exhaust Tube |
| $190r^2$ | External Radius of Exhaust Tube |
| 199 | Exhaust Channel of Exhaust Tube |
| x | Longitudinal Axis of Disinfection Chamber |
| V | Spiral Vortex Flow of Air |

Definitions

As utilized herein, including the claims, the phrase "radial thickness of the disinfection chamber" means the difference between the internal radius $122R^1$ of the housing 122 and the external radius $190r^2$ of the exhaust tube 190. The radial thickness of a cylindrical chamber 129 remains constant along the longitudinal length x of the chamber 129, while the radial thickness of a conical chamber 129 increases along the longitudinal length x of the chamber 129 from one end of the chamber 129 to the other.

Construction

Figure 1:
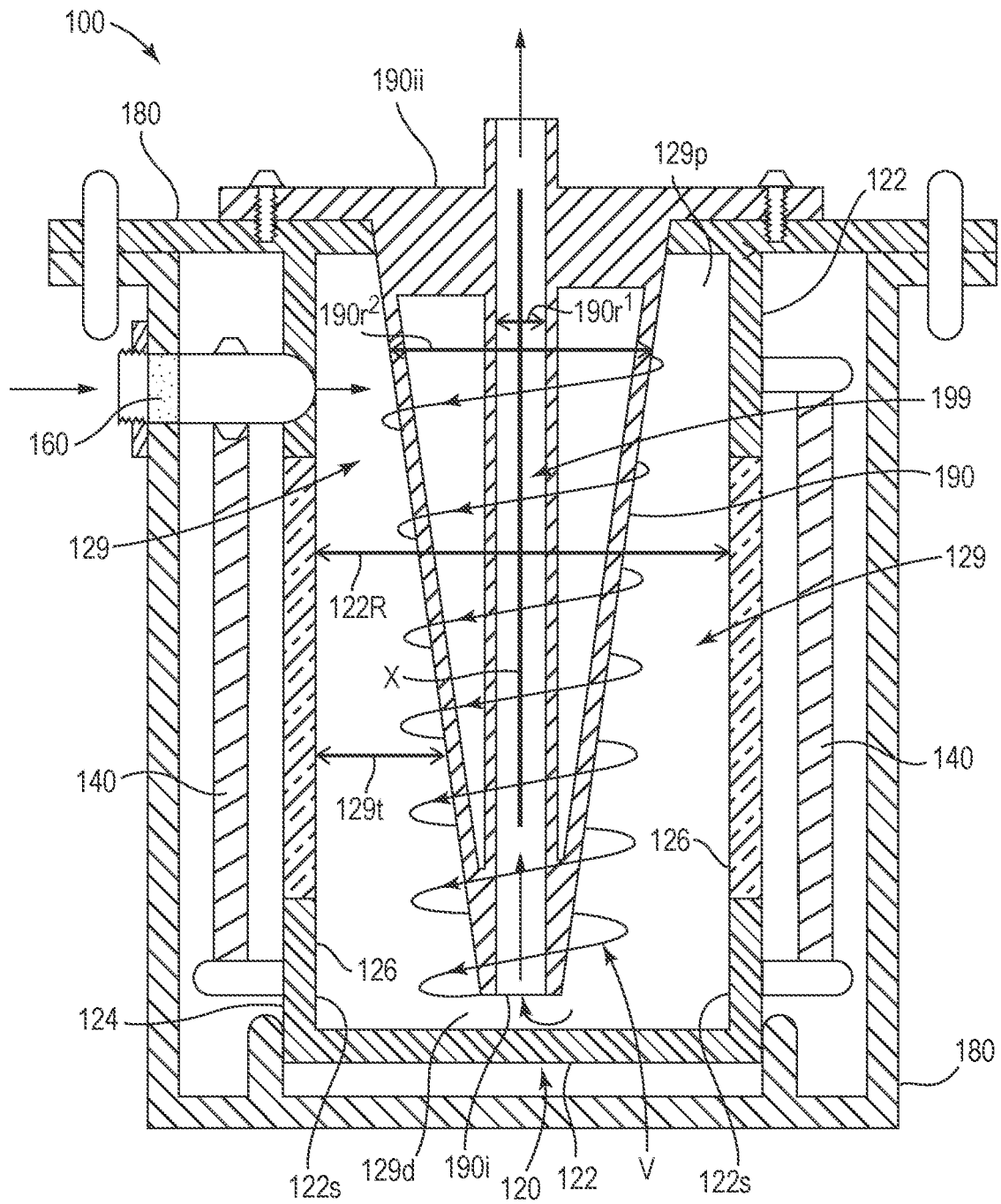
FIG. 1 is a schematic side view of one embodiment of the invention with portions thereof depicted in cross-section to facilitate viewing of internal components and air flow into and through the disinfection chamber.
Figure 2:
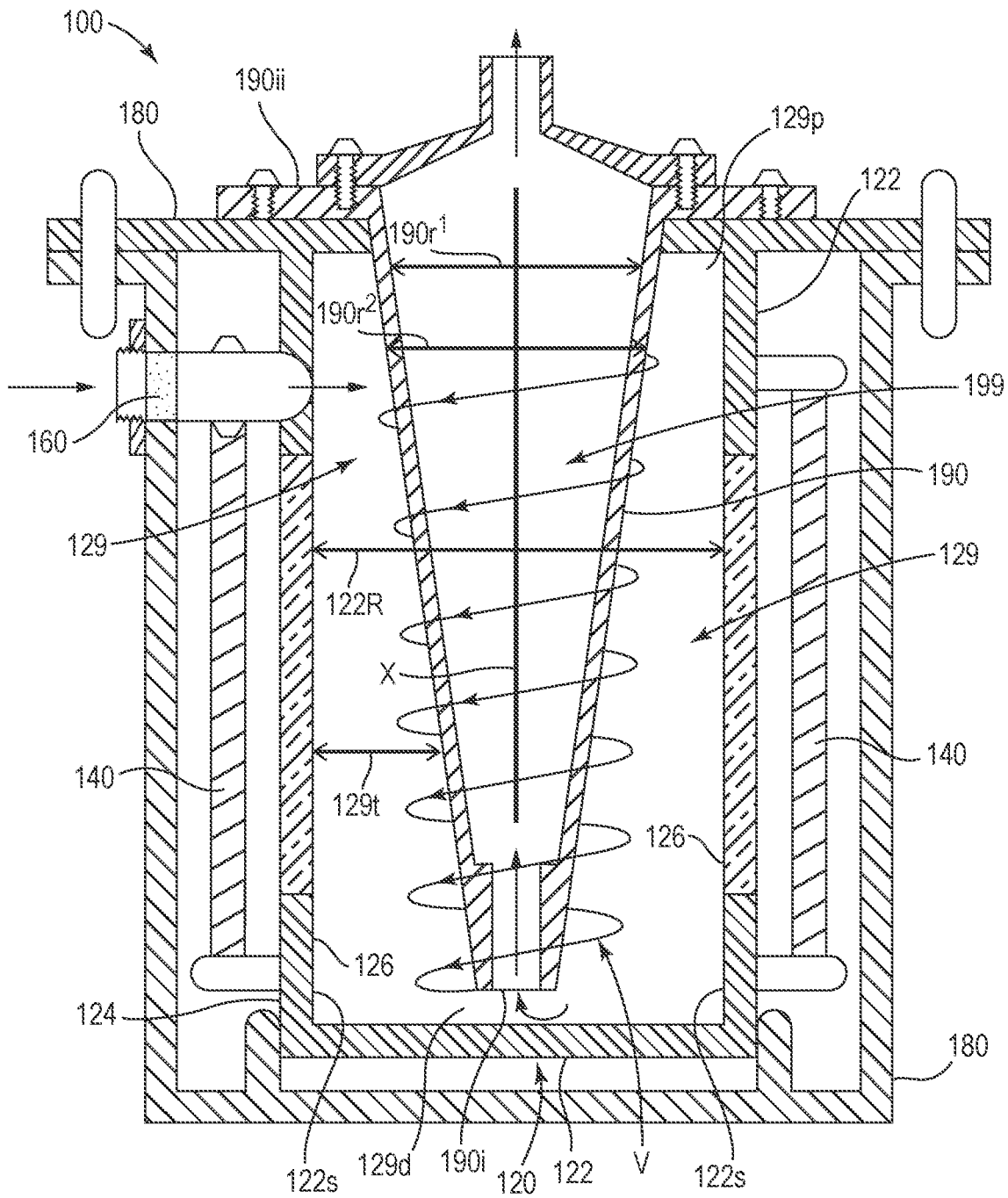
FIG. 2 is a schematic side view of another embodiment of the invention with portions thereof depicted in cross-section to facilitate viewing of internal components and air flow into and through the disinfection chamber.

Referring to FIGS. 1 and 2, the ultra violet air disinfectant machine 100 includes a cyclone separator 120 and at least one source of germicidal ultraviolet radiation 140. The ultra violet air disinfectant machine 100 also includes a means for moving air into and creating a spiral vortex air flow through the cyclone separator 120, such as a fan 160.

Cyclone separators 120 are widely used to remove particulates from an air, gas or liquid stream without the use of filters through vortex separation. A high speed rotating air flow known as a spiral vortex is established within a cylindrical or conical chamber 129, beginning at the proximal end 129p of the chamber 129 and ending at the distal end 129d of the chamber 129 before exiting the chamber 129 in a straight stream along the longitudinal axis x of the chamber 129 and out the proximal end 129p.

When used as a separator, inertia causes the larger (denser) particles entrained in the spiral vortex to strike the sidewall of the chamber, thereby loosing momentum and falling to the bottom of the chamber where they can be removed. In a conical system (i.e., internal radius $122R^1$ of the housing 122 defining the chamber 129 decreases from the proximal end 129p to the distal end 129d of the chamber 129) as the spiral vortex moves towards the narrow end of the chamber 129 the rotational radius of the vortex decreases, increasing inertial force and thus separating smaller and smaller particles.

The cyclone separator 120 component of the ultraviolet air disinfectant machine 100 is not employed to separate particles from an air stream but rather enhance UV disinfection of air flowing into and through the chamber 129. The spiral vortex air flow V produced in the chamber 129 serves to (i) concentrate the relatively heavier microorganisms in the air stream at the outside of the spiral vortex V, proximate the sidewall 124 of the cyclone separator 120 and closer to the source of disinfecting UV radiation 140, and (ii) increases dwell time of air within the chamber 129 so as to increase time of exposure of any microbes in the air to disinfecting UV radiation emanating from the at least one source of germicidal ultraviolet radiation 140.

Referring to FIGS. 1 and 2, in a conical disinfection system the radial thickness 129t of the disinfection chamber 129 increases, in a continuous, discontinuos or stepped fashion but preferably in a continuous fashion, from the proximal end 129p to the distal end 129d of the disinfection chamber 129, slowing the velocity of the spiral vortex airflow as the vortex spirals towards the distal end 129d of the disinfection chamber 129 while maintaining the desired spiral vortex flow so as to further increase disinfecting dwell time of the air within the disinfection chamber 129.

Referring to FIGS. 1 and 2, an exhaust tube 190 can extend along the longitudinal axis x of the disinfection chamber 129 with an inlet end 190i proximate the distal end 129d of the disinfection chamber 129 for accepting disinfected air reaching the distal end 129d of the disinfection chamber 129 and an outlet end 190ii proximate the proximal end 129p of the disinfection chamber 129 and extending through the housing 122 for venting disinfected air to the surrounding environment. FIG. 1 depicts a cylindrical exhaust channel 199 of uniform radius 190$r^2$ extending along the longitudinal x axis of the disinfection chamber 129 from the inlet end 190i of the exhaust tube 190 to the outlet end 190ii of the exhaust tube 190, while FIG. 2 depicts a conical exhaust channel 199 of increasing radius 190$r^2$ extending along the longitudinal x axis of the disinfection chamber 129 from the inlet end 190i of the exhaust tube 190 to proximate the outlet end 190ii of the exhaust tube 190.

The at least one source of germicidal ultraviolet radiation 140 (e.g., one or more axially extending UV bulbs) is positioned external to the housing 122 defining the disinfection chamber 129. The at least one source of germicidal ultraviolet radiation 140 is configured to emit germicidal ultraviolet radiation, preferably UVC, towards and into the disinfection chamber 129. The ultraviolet air disinfectant machine 100 preferably includes a plurality of sources of germicidal ultraviolet radiation 140 uniformly spaced about the disinfection chamber 129 (e.g., axially elongated UV bulbs 140 circumferentially spaced around the disinfection chamber 129 as depicted in FIG. 1).

In order for the UV radiation to reach the disinfecting chamber 129, the housing itself 122 or windows 126 through the housing 126 need to be transparent to the UV radiation emitted by the at least one source of germicidal ultraviolet radiation 140. Suitable materials include specifically but not exclusively, certain high purity polymers and copolymers such as cyclic olefin copolymers available from TOPAS Advanced Polymers GmbH based in Germany. Preferably, the housing 122 is equipped with UV transparent windows 126 radially aligned with each source of germicidal ultraviolet radiation 140, with the housing 126 or a lining on the interior sidewall surface 122s of the housing 126 reflective to UV radiation in order to maintain the UV radiation that entered into the disinfection chamber 129 through the UV transparent windows 126 within the disinfection chamber 129 and available for killing microbes entrained within the air passing through the disinfection chamber 129. Suitable UV reflective materials include specifically but not exclusively, aluminum and stainless steel. The exhaust tube 190 can also be reflective of germicidal ultraviolet radiation.

A UV reflective shroud 180 can enclose the cyclone separator 120 and the at least one source of germicidal ultraviolet radiation 140 to promote disinfection by redirecting and stray UV radiation towards the disinfection chamber 129 and also protect any humans from exposure to the UV radiation. The shroud 180 can also enclose the fan 160 so as to enhance the visual appeal of the machine 100 and/or dampen the noise generated by the fan 160.

Referring to FIGS. 1 and 2, the exhaust tube 190 can be removably bolted to an end of the housing 120 for allowing periodic detachment, withdrawal, and reattachment of the exhaust tube 190 to facilitate (i) cleaning of the inner sidewall surface 122s of the housing 120 including the interior surface of the UVC transparent window 126, (ii) cleaning of the exterior surface (unnumbered) of the exhaust tube 190, and/or (iii) replacement of the exhaust tube 190. Referring to FIG. 2, the outlet end 190ii of the exhaust tube 190 can be removably bolted to the balance of the exhaust tube 190 for providing access to the inner sidewall surface (unnumbered) of the exhaust tube 190 for cleaning.

Positioning the source of germicidal ultraviolet radiation 140 external to the housing 122 prevents the source of germicidal ultraviolet radiation 140 from interfering with the spiral vortex V flow through the disinfection chamber 129. Such interference would cause turbulence in the air flow pattern through the disinfection chamber 129, thereby reducing the desired concentration of microorganisms at the outside of the spiral vortex V closest to the source of germicidal ultraviolet radiation 140, and reducing dwell time within the chamber 129.

I claim:

1. An ultra violet air disinfectant machine, comprising:
   (a) a cyclone separator having a housing reflective of germicidal ultraviolet radiation with at least one window therethrough transparent to ultraviolet radiation and defining a disinfection chamber, the cyclone separator configured and arranged for effecting a spiral vortex flow of air through the disinfection chamber about a longitudinal axis of the disinfection chamber from an inlet port proximate a first longitudinal end of the disinfection chamber for introduction of environmental air into the disinfection chamber proximate a first longitudinal end of the disinfection chamber to an outlet port proximate a second longitudinal end of the disinfection chamber opposite the first longitudinal end for withdrawal of disinfected air from the disinfection chamber proximate the second longitudinal end of the disinfection chamber and discharge of the disinfected air to the surrounding environment, the imposed spiral vortex flow operable for inertial concentration of microbes in the spiral vortex flow of air proximate a sidewall of the cyclone separator and past the at least one window, and
   (b) at least one source of germicidal ultraviolet radiation positioned external to the housing for emitting germicidal ultraviolet radiation into the disinfection chamber through the window.

2. The ultra violet air disinfectant machine of claim 1 further comprising a fan for creating an air flow into the disinfection chamber to create the spiral vortex flow of air.

3. The ultra violet air disinfectant machine of claim 2 wherein the cyclone separator, the at least one source of germicidal ultraviolet radiation and the fan are enclosed within a shroud.

4. The ultra violet air disinfectant machine of claim 1 wherein the cyclone separator and the at least one source of germicidal ultraviolet radiation are enclosed within a shroud.

5. The ultra violet air disinfectant machine of claim 1 wherein the machine includes a plurality of peripherally spaced separate and independent sources of germicidal ultraviolet radiation and a plurality of peripherally spaced windows with each source of germicidal ultraviolet radiation paired and axially aligned with one of the windows for emitting germicidal ultraviolet radiation into the disinfection chamber through the paired window.

6. The ultra violet air disinfectant machine of claim 1 wherein air enters the disinfection chamber proximate a proximal end of the disinfection chamber, and the ultra violet air disinfectant machine further comprises an axially extending exhaust tube having an inlet end proximate a distal end of the disinfection chamber for accepting air flow from the disinfection chamber and an outlet end proximate the proximal end of the disinfection chamber for venting air flow to the environment.

7. The ultra violet air disinfectant machine of claim 6 wherein the exhaust tube is reflective of germicidal ultraviolet radiation.

8. The ultra violet air disinfectant machine of claim 6 wherein the exhaust tube is selectively detachable from the housing for at least one of (i) providing cleaning access to the interior surface of the housing, (ii) providing cleaning access to the exterior surface of the exhaust tube, and (iii) replacing the exhaust tube.

9. The ultra violet air disinfectant machine of claim 6 wherein the disinfection chamber is a hollow cylinder or a hollow frustum of a cone wherein the radial thickness t of the disinfection chamber at any point along the longitudinal axial length of the disinfection chamber is the difference between the internal radius R of the housing and the external radius r of the exhaust tube, and the radial thickness t of the disinfection chamber increases from the proximal end of the disinfection chamber to the distal end of the disinfection chamber.

10. The ultra violet air disinfectant machine of claim 9 wherein the increasing radial thickness is continuous.

11. The ultra violet air disinfectant machine of claim 9 wherein the increasing radial thickness is discontinuous.

12. The ultra violet air disinfectant machine of claim 9 wherein the increasing radial thickness is stepped.

13. An ultra violet air disinfectant machine, comprising:
(a) a cyclone separator having a housing reflective of germicidal ultraviolet radiation with at least one window therethrough transparent to ultraviolet radiation and defining a cylindrical or conical disinfection chamber, the cyclone separator configured and arranged for effecting a spiral vortex flow of air through the disinfection chamber about a longitudinal axis of the disinfection chamber from an inlet port proximate a first longitudinal end of the disinfection chamber for introduction of environmental air into the disinfection chamber to an outlet port proximate a second longitudinal end of the disinfection chamber opposite the first longitudinal end for withdrawal of disinfected air from the disinfection chamber, and the housing having a smoothly curved inner sidewall surface for promoting laminar flow within the spiral vortex, and
(b) at least one source of germicidal ultraviolet radiation positioned external to the housing for emitting germicidal ultraviolet radiation into the disinfection chamber through the window.

14. The ultra violet air disinfectant machine of claim 13 wherein the cyclone separator is free of baffles extending into the disinfection chamber.

15. The ultra violet air disinfectant machine of claim 13 further comprising a fan for creating an air flow into the disinfection chamber to create the spiral vortex flow of air.

16. The ultra violet air disinfectant machine of claim 15 wherein the cyclone separator, the at least one source of germicidal ultraviolet radiation and the fan are enclosed within a shroud.

17. The ultra violet air disinfectant machine of claim 13 wherein the cyclone separator and the at least one source of germicidal ultraviolet radiation are enclosed within a shroud.

18. The ultra violet air disinfectant machine of claim 13 wherein the machine includes a plurality of peripherally spaced separate and independent sources of germicidal ultraviolet radiation and a plurality of peripherally spaced windows with each source of germicidal ultraviolet radiation paired and axially aligned with one of the windows for emitting germicidal ultraviolet radiation into the disinfection chamber through the paired window.

19. The ultra violet air disinfectant machine of claim 13 wherein air enters the disinfection chamber proximate a proximal end of the disinfection chamber, and the ultra violet air disinfectant machine further comprises an axially extending exhaust tube having an inlet end proximate a distal end of the disinfection chamber for accepting air flow from the disinfection chamber and an outlet end proximate the proximal end of the disinfection chamber for venting air flow to the environment.

20. The ultra violet air disinfectant machine of claim 19 wherein the disinfection chamber is a hollow cylinder or a hollow frustum of a cone wherein the radial thickness t of the disinfection chamber at any point along the longitudinal axial length of the disinfection chamber is the difference between the internal radius R of the housing and the external radius r of the exhaust tube, and the radial thickness t of the disinfection chamber increases from the proximal end of the disinfection chamber to the distal end of the disinfection chamber.

21. The ultra violet air disinfectant machine of claim 20 wherein the increasing radial thickness is continuous.

22. The ultra violet air disinfectant machine of claim 20 wherein the increasing radial thickness is discontinuous.

23. The ultra violet air disinfectant machine of claim 20 wherein the increasing radial thickness is stepped.

24. The ultra violet air disinfectant machine of claim 13 wherein the exhaust tube is reflective of germicidal ultraviolet radiation.

* * * * *